US010416477B2

(12) United States Patent
Wiser et al.

(10) Patent No.: US 10,416,477 B2
(45) Date of Patent: *Sep. 17, 2019

(54) OPHTHALMIC SYSTEM HAVING ADJUSTABLE ACCOMMODATION BASED ON PHOTODETECTION

(71) Applicant: Verily Life Sciences LLC, Mountain View, CA (US)

(72) Inventors: Robert F. Wiser, San Francisco, CA (US); Jennifer Han, Palo Alto, CA (US); Brian Otis, Saratoga, CA (US); Nathan Pletcher, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/891,031

(22) Filed: Feb. 7, 2018

(65) Prior Publication Data

US 2018/0164607 A1 Jun. 14, 2018

Related U.S. Application Data

(63) Continuation of application No. 14/737,363, filed on Jun. 11, 2015, now Pat. No. 9,933,634.

(Continued)

(51) Int. Cl.
*G02C 7/02* (2006.01)
*G02C 7/04* (2006.01)
(Continued)

(52) U.S. Cl.
CPC .............. *G02C 7/083* (2013.01); *A61B 3/113* (2013.01); *G02B 27/0093* (2013.01);
(Continued)

(58) Field of Classification Search
CPC ........ G02C 7/083; G02C 7/049; G02C 7/024; G02C 7/04; G02C 7/02; G02C 7/022; G02C 7/041; A61B 3/113; G02B 27/0093
(Continued)

(56) References Cited

U.S. PATENT DOCUMENTS 4,391,215 A 7/1983 Sansone
4,913,546 A 4/1990 Shinji et al.
(Continued)

FOREIGN PATENT DOCUMENTS

EP 2620802 A1 7/2013
EP 2 647 336 A1 10/2013
(Continued)

OTHER PUBLICATIONS

First Office Action for Chinese Patent Application No. 201580031767.3, dated Jul. 23, 2018, 12 pages.
(Continued)

*Primary Examiner* — Jordan M Schwartz
(74) *Attorney, Agent, or Firm* — Christensen O'Connor Johnson Kindness PLLC

(57) ABSTRACT

Techniques and mechanisms for determining an amount of accommodation for an ophthalmic system are described. In an embodiment, the ophthalmic system includes a first circuit and a second circuit, each comprising a respective photodiode. The second circuit is configured to provide a light response profile that is more linear than a light response profile provided by the first circuit. Light sensing by the first circuit results in generation of a first signal indicating a level of ambient light in a surrounding environment. Other light sensing by the second circuit results in a second signal being generated. An amount of accommodation is determined based at least in part on the second signal.

18 Claims, 8 Drawing Sheets

Related U.S. Application Data

(60) Provisional application No. 62/012,005, filed on Jun. 13, 2014.

(51) Int. Cl.
*G02C 7/08* (2006.01)
*A61B 3/113* (2006.01)
*G02B 27/00* (2006.01)

(52) U.S. Cl.
CPC .............. *G02C 7/024* (2013.01); *G02C 7/04* (2013.01); *G02C 7/049* (2013.01)

(58) Field of Classification Search
USPC ....................................... 351/159.03, 159.02
See application file for complete search history.

(56) References Cited

U.S. PATENT DOCUMENTS

| | | | |
|---|---|---|---|
| 5,767,538 | A | 6/1998 | Mullins et al. |
| 7,183,531 | B2 | 2/2007 | Olsen et al. |
| 7,224,858 | B2 | 5/2007 | Welch et al. |
| 7,645,978 | B2 | 1/2010 | Kamon |
| 8,213,022 | B1 | 7/2012 | Riza et al. |
| 8,608,310 | B2 | 12/2013 | Otis et al. |
| 8,636,358 | B2 | 1/2014 | Binder |
| 8,786,675 | B2 | 7/2014 | Deering |
| 8,960,898 | B1 | 2/2015 | Etzkorn et al. |
| 9,323,073 | B2 | 4/2016 | Pugh et al. |
| 9,690,118 | B2 | 6/2017 | Etzkorn et al. |
| 10,268,051 | B2 | 4/2019 | Etzkorn et al. |
| 2005/0073739 | A1 | 4/2005 | Meredith et al. |
| 2006/0184245 | A1 | 8/2006 | Graf et al. |
| 2007/0153405 | A1 | 7/2007 | Kuiper et al. |
| 2008/0208335 | A1 | 8/2008 | Blum et al. |
| 2012/0133891 | A1* | 5/2012 | Jiang .................. H04N 5/3535 351/210 |
| 2012/0140167 | A1 | 6/2012 | Blum |
| 2012/0236417 | A1 | 9/2012 | Pugh et al. |
| 2012/0245444 | A1 | 9/2012 | Otis et al. |
| 2012/0310339 | A1 | 12/2012 | Berge |
| 2013/0063550 | A1 | 3/2013 | Ritchey et al. |
| 2013/0258275 | A1* | 10/2013 | Toner .................. G02C 7/04 351/159.03 |
| 2013/0258287 | A1 | 10/2013 | Pugh et al. |
| 2014/0081178 | A1* | 3/2014 | Pletcher .................. G02C 7/04 600/595 |
| 2014/0085600 | A1 | 3/2014 | Pletcher et al. |
| 2014/0107447 | A1 | 4/2014 | Liu et al. |
| 2014/0107448 | A1 | 4/2014 | Liu et al. |
| 2014/0156000 | A1 | 6/2014 | Campin et al. |
| 2014/0192311 | A1 | 7/2014 | Pletcher et al. |
| 2014/0192312 | A1 | 7/2014 | Pletcher et al. |
| 2014/0192318 | A1 | 7/2014 | Guth et al. |
| 2014/0194773 | A1 | 7/2014 | Pletcher et al. |
| 2014/0209481 | A1 | 7/2014 | Pletcher et al. |
| 2014/0213867 | A1 | 7/2014 | Pletcher et al. |
| 2014/0240655 | A1 | 8/2014 | Pugh et al. |
| 2014/0240657 | A1 | 8/2014 | Pugh et al. |
| 2014/0243971 | A1 | 8/2014 | Pugh et al. |
| 2014/0327875 | A1 | 11/2014 | Blum et al. |
| 2014/0340630 | A1 | 11/2014 | Pugh et al. |
| 2015/0182116 | A1 | 7/2015 | Pletcher et al. |
| 2016/0299354 | A1 | 10/2016 | Shtukater |
| 2016/0345818 | A1 | 12/2016 | Suzuki et al. |
| 2017/0023793 | A1 | 1/2017 | Shtukater |

FOREIGN PATENT DOCUMENTS

| | | |
|---|---|---|
| EP | 2772792 A1 | 9/2014 |
| EP | 2846183 A2 | 3/2015 |
| EP | 3155477 A1 | 4/2017 |
| JP | 2002-282209 A | 10/2002 |
| JP | 2008-263547 A | 10/2008 |
| JP | 2010-517081 A | 5/2010 |
| JP | 2010-517082 T | 5/2010 |
| JP | 2014-21500 A | 2/2014 |
| WO | 2003017203 A1 | 2/2003 |
| WO | 2005000395 A1 | 1/2005 |
| WO | 2007107589 A1 | 9/2007 |
| WO | 2008091859 A1 | 7/2008 |
| WO | 2009108753 A1 | 9/2009 |
| WO | 2011016860 A1 | 2/2011 |
| WO | 2012061411 A1 | 5/2012 |
| WO | 2013086078 A1 | 6/2013 |
| WO | 2014043614 A1 | 3/2014 |
| WO | 2015/191247 A1 | 12/2015 |

OTHER PUBLICATIONS

Notice of Reasons for Rejections for Japanese Patent Application No. 2016-567515, dated Oct. 2, 2018, 13 pages.
Examination Report for European Patent Application No. 15807226.4, dated Nov. 13, 2018, 5 pages.
PCT/US2016/045376—International Search Report and Written Opinion, dated Dec. 2, 2016, 13 pages.
Notice of Reasons for Rejection for Japanese Application 2016-567515, dated Jan. 5, 2018, 6 pages.
Extended European Search Report for EP Application 15807295.9, dated Nov. 29, 2017, 8 pages.
Examination Report No. 1 for AU 2015275156 dated Sep. 11, 2017, 3 pages.
PCT/US2015/035661—International Preliminary Report on Patentability, dated Dec. 22, 2016, 7 pages.
PCT/US2015/035661—International Search Report and Written Opinion, dated Aug. 25, 2015, 10 pages.
Decision of Grant issued for Russian application No. 2017100465, dated Mar. 2, 2018, 21 pages.
First Examination Report for Indian Patent Application No. 201647040760 dated Feb. 21, 2019, 7 pages.
Decision of Dismissal of Amendment mailed May 29, 2019, issued in corresponding Japanese Application No. 2016-567515, filed Jun. 12, 2015, 5 pages.
Decision of Rejection dated Jun. 4, 2019, issued in corresponding Japanese Application No. 2016-567925, filed Jun. 12, 2015, 3 pages.
Examination Report dated May 30, 2019, issued in corresponding Canadian Application No. 2,950,560, filed May 18, 2015, 3 pages.

* cited by examiner

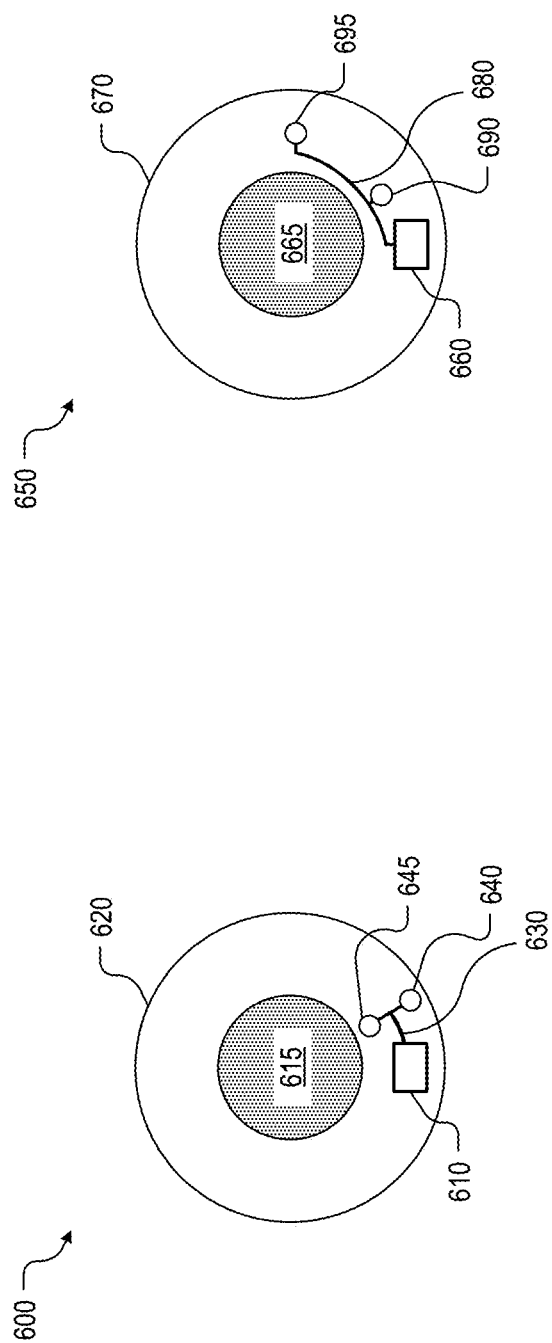

OPHTHALMIC SYSTEM HAVING ADJUSTABLE ACCOMMODATION BASED ON PHOTODETECTION

CROSS REFERENCE TO RELATED APPLICATIONS

This application is a continuation application of U.S. patent application Ser. No. 14/737,363, filed on Jun. 11, 2015, which claims priority under the provisions of 35 U.S.C. § 119(e) to U.S. Provisional Application No. 62/012,005 filed Jun. 13, 2014, the contents both of which are hereby incorporated by reference.

BACKGROUND

1. Technical Field

This disclosure relates generally to the field of optics, and in particular but not exclusively, relates to contact lenses.

2. Background Art

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages.

Recent technologies have begun to provide for various devices that operate in or on a human eye to aid the visual focus of a user. For some types of these devices, an accommodating lens includes one or more elements and circuitry to apply an electrical signal to change a focusing power of the one or more elements. Determining when to change such focusing power is often based on a direction of a gaze by a user of the optical device. As the capabilities of accommodation-capable optical devices continue to increase, there is expected to be an increased demand for such optical devices to provide accurate tracking of direction of gaze by a user.

BRIEF DESCRIPTION OF THE DRAWINGS

The various embodiments of the present invention are illustrated by way of example, and not by way of limitation, in the figures of the accompanying drawings and in which:

FIGS. 6A and 6B illustrate different photodetector layouts on an eye-mountable device for a gaze tracking system, each in accordance with a corresponding embodiment of the disclosure.

DETAILED DESCRIPTION

Figure 1:
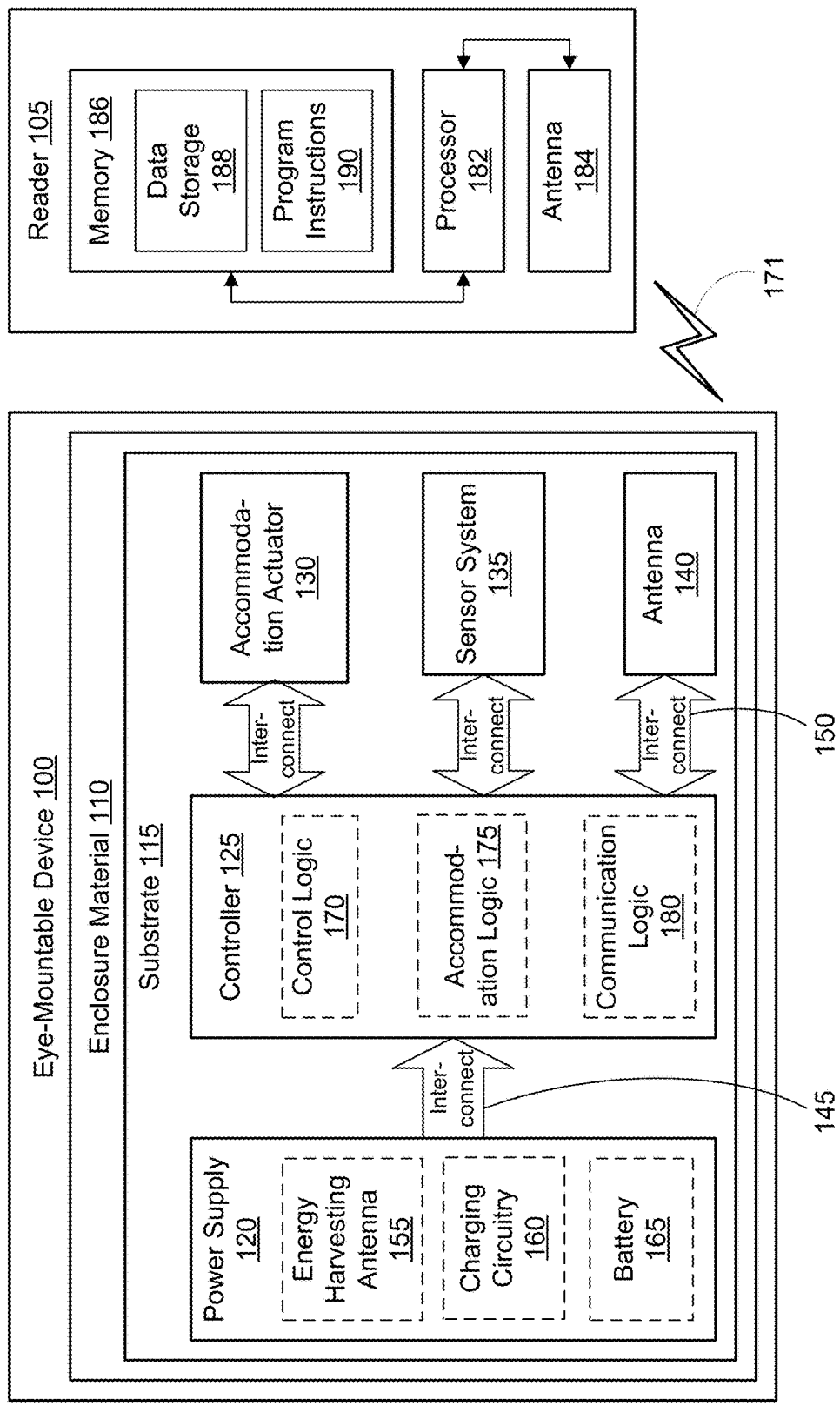
FIG. 1 is a functional block diagram of an eye-mountable device with gaze tracking for auto-accommodation along with an external reader, in accordance with an embodiment of the disclosure.

Embodiments of an apparatus, system and methods of operation for a contact lens with gaze tracking based on photodetection are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Described herein is a smart contact lens or other eye-mountable device that includes gaze detection circuitry and logic for identifying the direction or focal distance of a user's gaze and using this information, for example, for real-time feedback control of an accommodation actuator. Embodiments of the eye-mountable device may include power supply circuitry, control electronics, an accommodation actuator, a light sensor system, and an antenna all embedded within an enclosure material formed to be contact mounted to an eye. The control electronics are coupled to monitor the light sensor system to identify gaze direction/focal distance, manipulate the accommodation actuator to control the optical power of the eye-mountable device, and provide wireless communications with an external reader. In some embodiments, the power supply may include charging circuitry for controlling inductive wireless charging of an embedded battery.

The enclosure material may be fabricated of a variety of materials compatible for direct contact with a human eye, such as a polymeric material, a hydrogel, PMMA, silicone based polymers (e.g., fluoro-silicon acrylate), or otherwise. The enclosure material may be in the form of a round lens with a concave curvature configured to mount to a corneal surface of an eye. The electronics may be disposed upon a substrate embedded within the enclosure material near its periphery to avoid interference with incident light received closer to the central region of the cornea. The light sensor system may be arranged on the substrate to face outward towards the eyelids to detect the gaze direction/focal distance based upon the amount and position of eyelid coverage over the light sensor system. As the eyelids cover different portions of the light sensor system, this changes its exposure to ambient light of a surrounding environment, which may be measured to determine gaze direction and/or focal distance.

In some embodiments, the gaze direction/focal distance information may then be used to determine the amount of accommodation to be applied via a see-through accommodation actuator positioned in a central portion of the enclosure material. The accommodation actuator is coupled to the controller to be electrically manipulated thereby. For example, the accommodation actuator may be implemented with a liquid crystal cell that changes its index of refraction in response to an applied electrical bias signal. In other embodiments, the accommodation actuator may be implemented using other types of electro-active optical materials such as electro-optic materials that vary refractive index in the presence of an applied electric field or electro-mechanical structures that change the shape of a deformable lens. Other example structures that may be used to implement the accommodation actuator include electro-wetting optics, micro-electro-mechanical systems, or otherwise.

Certain embodiments provide for improved accuracy of gaze detection during any of a variety of levels of environmental lighting. During a typical day, a person can expect to experience different levels of ambient light that vary, for example, by up to four or five orders of magnitude. Such a widely varied lighting conditions are accommodated, according to different embodiments, by using one photodetector circuit of an EMD to configure a biasing, gain or other operational characteristic of another photodetector circuit of the EMD.

FIG. 1 is a functional block diagram of an eye-mountable device 100 with gaze tracking for auto-accommodation along with an external reader 105, in accordance with an embodiment of the disclosure. The exposed portion of eye-mountable device 100 is an enclosure material 110 formed to be contact-mounted to a corneal surface of an eye. A substrate 115 is embedded within or surrounded by enclosure material 110 to provide a mounting surface for a power supply 120, a controller 125, an accommodation actuator 130, a sensor system 135, an antenna 140, and various interconnects 145 and 150. The illustrated embodiment of power supply 120 includes an energy harvesting antenna 155, charging circuitry 160, and a battery 165. The illustrated embodiment of controller 125 includes control logic 170, accommodation logic 175, and communication logic 180. The illustrated embodiment of reader 105 includes a processor 182, an antenna 184, and memory 186. The illustrated embodiment of memory 186 includes data storage 188 and program instructions 190.

Controller 125 is coupled to receive feedback control signals from sensor system 135 and further coupled to operate accommodation actuator 130. Power supply 120 supplies operating voltages to the controller 125 and/or the accommodation actuator 130. Antenna 140 is operated by the controller 125 to communicate information to and/or from eye-mountable device 100. In one embodiment, antenna 140, controller 125, power supply 120, and sensor system 135 are all situated on the embedded substrate 115. In one embodiment, accommodation actuator 130 is embedded within enclosure material 110, but is not disposed on substrate 115. Because eye-mountable device 100 includes electronics and is configured to be contact-mounted to an eye, it is also referred to herein as an ophthalmic electronics platform, contact lens, or smart contact lens.

To facilitate contact-mounting, the enclosure material 110 may have a concave surface configured to adhere ("mount") to a moistened corneal surface (e.g., by capillary forces with a tear film coating the corneal surface). Additionally or alternatively, the eye-mountable device 100 may be adhered by a vacuum force between the corneal surface and enclosure material 110 due to the concave curvature. While mounted with the concave surface against the eye, the outward-facing surface of the enclosure material 110 may have a convex curvature that is formed to not interfere with eye-lid motion while the eye-mountable device 100 is mounted to the eye. For example, the enclosure material 110 may be a substantially transparent curved disk shaped similarly to a contact lens.

Enclosure material 110 may include one or more biocompatible materials, such as those employed for use in contact lenses or other ophthalmic applications involving direct contact with the corneal surface. Enclosure material 110 may optionally be formed in part from such biocompatible materials or may include an outer coating with such biocompatible materials. Enclosure material 110 may include materials configured to moisturize the corneal surface, such as hydrogels and the like. In some instances, enclosure material 110 may be a deformable ("non-rigid") material to enhance wearer comfort. In some instances, enclosure material 110 may be shaped to provide a predetermined, vision-correcting optical power, such as can be provided by a contact lens. Enclosure material may be fabricated of various materials including a polymeric material, a hydrogel, PMMA, silicone based polymers (e.g., fluoro-silicon acrylate), or otherwise.

Substrate 115 includes one or more surfaces suitable for mounting the sensor system 135, controller 125, power supply 120, and antenna 140. Substrate 115 may be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) may be patterned on substrate 115 to form circuitry, electrodes, etc. For example, antenna 140 may be formed by depositing a pattern of gold or another conductive material on substrate 115. Similarly, interconnects 145 and 150 may be formed by depositing suitable patterns of conductive materials on substrate 115. A combination of resists, masks, and deposition techniques may be employed to pattern materials on substrate 115. Substrate 115 may be a relatively rigid material, such as polyethylene terephthalate ("PET") or another material sufficient to structurally support the circuitry and/or electronics within enclosure material 110. Eye-mountable device 100 may alternatively be arranged with a group of unconnected substrates rather than a single substrate. For example, controller 125 and power supply 120 may be mounted to one substrate, while antenna 140 and sensor system 135 are mounted to another substrate and the two may be electrically connected via interconnects.

In some embodiments, power supply 120 and controller 125 (and the substrate 115) may be positioned away from the center of eye-mountable device 100 and thereby avoid interference with light transmission to the eye through the center of eye-mountable device 110. In contrast, accommodation actuator 130 may be centrally positioned to apply optical accommodation to the light transmitted to the eye through the center of eye-mountable device 110. For example, where eye-mountable device 100 is shaped as a concave-curved disk, substrate 115 may be embedded around the periphery (e.g., near the outer circumference) of the disk. In some embodiments, sensor system 135 includes two or more discrete photodetector sensors that are distributed to sense the eyelid overlap. Sensor system 135 and/or substrate 115 may be substantially transparent to incoming visible light to mitigate interference with light transmission to the eye.

Substrate 115 may be shaped as a flattened ring with a radial width dimension sufficient to provide a mounting platform for the embedded electronics components. Substrate 115 may have a thickness sufficiently small to allow the substrate to be embedded in enclosure material 110 without adversely influencing the profile of eye-mountable device 100. Substrate 115 may have a thickness sufficiently large to provide structural stability suitable for supporting the electronics mounted thereon. For example, substrate 115 may be shaped as a ring with a diameter of about 10 millimeters, a radial width of about 1 millimeter (e.g., an outer radius 1 millimeter larger than an inner radius), and a thickness of about 50 micrometers. Substrate 115 may optionally be aligned with the curvature of the eye-mounting surface of eye-mountable device 100 (e.g., convex surface). For example, substrate 115 may be shaped along the surface of an imaginary cone between two circular segments that define an inner radius and an outer radius. In such an example, the surface of substrate 115 along the surface of the imaginary cone defines an inclined surface that is approximately aligned with the curvature of the eye mounting surface at that radius.

In the illustrated embodiment, power supply 120 includes a battery 165 to power the various embedded electronics, including controller 125. Battery 165 may be inductively charged by charging circuitry 160 and energy harvesting antenna 155. In one embodiment, antenna 140 and energy harvesting antenna 155 are independent antennae, which serve their respective functions of energy harvesting and communications. In another embodiment, energy harvesting antenna 155 and antenna 140 are the same physical antenna that provide respective functions for time-shared or simultaneous inductive charging and wireless communications with reader 105. Additionally or alternatively, power supply 120 may include a solar cell ("photovoltaic cell") to capture energy from incoming ultraviolet, visible, and/or infrared radiation. Furthermore, an inertial power scavenging system may be included to capture energy from ambient vibrations.

Charging circuitry 160 may include a rectifier/regulator to condition the captured energy for charging battery 165 or directly power controller 125 without battery 165. Charging circuitry 160 may also include one or more energy storage devices to mitigate high frequency variations in energy harvesting antenna 155. For example, one or more energy storage devices (e.g., a capacitor, an inductor, etc.) may be connected to function as a low-pass filter.

Controller 125 contains logic to choreograph the operation of the other embedded components. Control logic 170 controls the general operation of eye-mountable device 100, including providing a logical user interface, power control functionality, etc. Accommodation logic 175 includes logic for monitoring feedback signals from sensor system 135, determining the current gaze direction or focal distance of the user, and manipulating accommodation actuator 130 in response to provide the appropriate accommodation. The auto-accommodation may be implemented in real-time based upon feedback from the gaze tracking, or permit user control to select specific accommodation regimes (e.g., near-field accommodation for reading, far-field accommodation for regular activities, etc.). Communication logic 180 provides communication protocols for wireless communication with reader 105 via antenna 140. In one embodiment, communication logic 180 provides backscatter communication via antenna 140 when in the presence of an electromagnetic field 171 output from reader 105. In one embodiment, communication logic 180 operates as a smart wireless radio-frequency identification ("RFID") tag that modulates the impedance of antenna 140 for backscatter wireless communications. The various logic modules of controller 125 may be implemented in software/firmware executed on a general purpose microprocessor, in hardware (e.g., application specific integrated circuit), or a combination of both.

Eye-mountable device 100 may include various other embedded electronics and logic modules. For example, a light source or pixel array may be included to provide visible feedback to the user. An accelerometer or gyroscope may be included to provide positional, rotational, directional or acceleration feedback information to controller 125.

It is noted that the block diagram shown in FIG. 1 is described in connection with functional modules for convenience in description, but does not necessarily connote physical organization. Rather, embodiments of eye-mountable device 100 may be arranged with one or more of the functional modules ("sub-systems") implemented in a single chip, multiple chips, in one or more integrated circuits, or otherwise.

External reader 105 includes an antenna 184 (or group of more than one antennae) to send and receive wireless signals 171 to and from eye-mountable device 100. External reader 105 also includes a computing system with a processor 182 in communication with a memory 186. Memory 186 is a non-transitory computer-readable medium that may include, without limitation, magnetic disks, optical disks, organic memory, and/or any other volatile (e.g. RAM) or non-volatile (e.g. ROM) storage system readable by the processor 182. Memory 186 may include a data storage 188 to store indications of data, such as data logs (e.g., user logs), program settings (e.g., to adjust behavior of eye-mountable device 100 and/or external reader 105), etc. Memory 186 may also include program instructions 190 for execution by processor 182 to cause the external reader 105 to perform processes specified by the instructions 190. For example, program instructions 190 may cause external reader 105 to provide a user interface that allows for retrieving information communicated from eye-mountable device 100 or allows transmitting information to eye-mountable device 100 to program or otherwise select operational modes of eye-mountable device 100. External reader 105 may also include one or more hardware components for operating antenna 184 to send and receive wireless signals 171 to and from eye-mountable device 100.

External reader 105 may be a smart phone, digital assistant, or other portable computing device with wireless connectivity sufficient to provide the wireless communication link 171. External reader 105 may also be implemented as an antenna module that can be plugged in to a portable computing device, such as in an example where the communication link 171 operates at carrier frequencies not commonly employed in portable computing devices. In some instances, external reader 105 is a special-purpose device configured to be worn relatively near a wearer's eye to allow the wireless communication link 171 to operate with a low power budget. For example, the external reader 105 may be integrated in a piece of jewelry such as a necklace, earring, etc. or integrated in an article of clothing worn near the head, such as a hat, headband, etc.

Figure 2A:
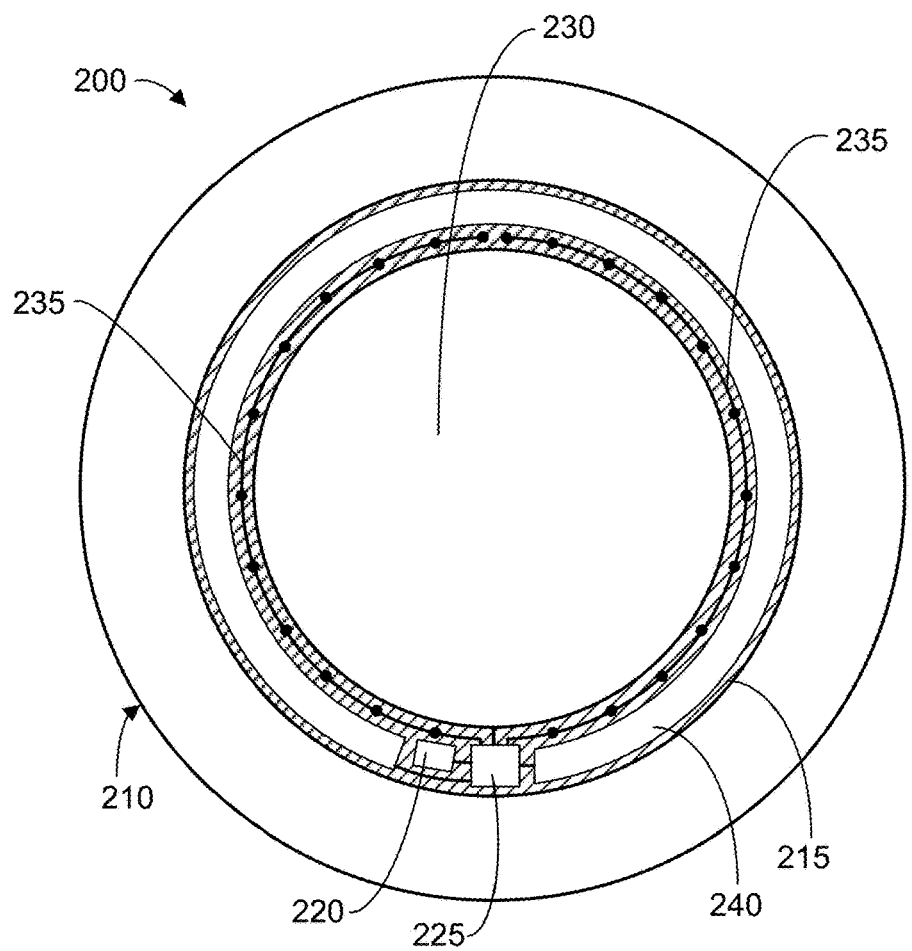
FIG. 2A is a top view of an eye-mountable device, in accordance with an embodiment of the disclosure.
Figure 2B:
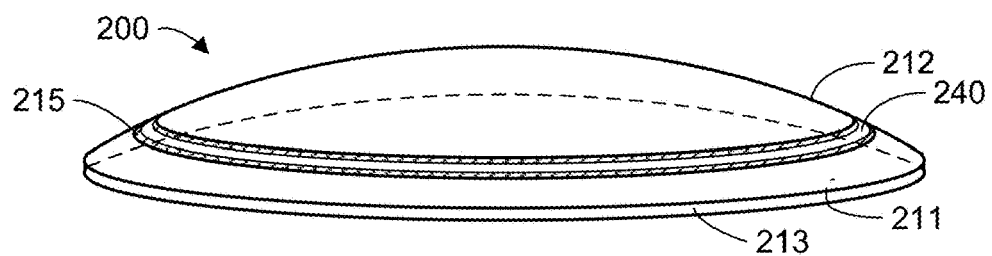
FIG. 2B is a perspective view of an eye-mountable device, in accordance with an embodiment of the disclosure.

FIGS. 2A and 2B illustrate two views of an eye-mountable device 200, in accordance with an embodiment of the disclosure. FIG. 2A is a top view of eye-mountable device 200 while FIG. 2B is a perspective view of the same. Eye-mountable device 200 is one possible implementation of eye-mountable device 100 illustrated in FIG. 1. The illustrated embodiment of eye-mountable device 200 includes an enclosure material 210, a substrate 215, a power supply 220, a controller 225, an accommodation actuator 230, a sensor system 235, and an antenna 240. It should be appreciated that FIGS. 2A and 2B are not necessarily drawn to scale, but have been illustrated for purposes of explanation only in describing the arrangement of the example eye-mountable device 200.

Enclosure material 210 of eye-mountable device 200 is shaped as a curved disk. Enclosure material 210 is a substantially transparent material to allow incident light to be transmitted to the eye while eye-mountable device 200 is mounted to the eye. Enclosure material 210 is a biocompatible material similar to those employed to form vision correction and/or cosmetic contact lenses in optometry, such as a polymeric material, polyethylene terephthalate ("PET"), polymethyl methacrylate ("PMMA"), polyhydroxyethylmethacrylate ("polyHEMA"), a hydrogel, silicon based polymers (e.g., fluoro-silicon acrylate) combinations of these, or otherwise. Enclosure material 210 may be formed with one side having a concave surface 211 suitable to fit over a corneal surface of an eye. The opposite side of the disk may have a convex surface 212 that does not interfere with eyelid motion while eye-mountable device 200 is mounted to the eye. In the illustrated embodiment, a circular or oval outer side edge 213 connects the concave surface 211 and convex surface 212.

Eye-mountable device 200 may have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of eye-mountable device 200 may be selected according to the size and/or shape of the corneal surface of the wearer's eye. Enclosure material 210 may be formed with a curved shape in a variety of ways. For example, techniques similar to those employed to form vision-correction contact lenses, such as heat molding, injection molding, spin casting, etc. can be employed to form enclosure material 210.

Substrate 215 is embedded within enclosure material 210. Substrate 215 may be embedded to be situated along the outer periphery of enclosure material 210, away from the central region where accommodation actuator 230 is positioned. In the illustrated embodiment, substrate 215 encircles accommodation actuator 230. Substrate 215 does not interfere with vision because it is too close to the eye to be in focus and is positioned away from the central region where incident light is transmitted to the light-sensing portions of the eye. In some embodiments, substrate 215 may optionally be formed of a transparent material to further mitigate effects on visual perception. Substrate 215 may be shaped as a flat, circular ring (e.g., a disk with a centered hole). The flat surface of substrate 215 (e.g., along the radial width) is a platform for mounting electronics and for patterning conductive materials to form electrodes, antenna(e), and/or interconnections.

Figure 3A:
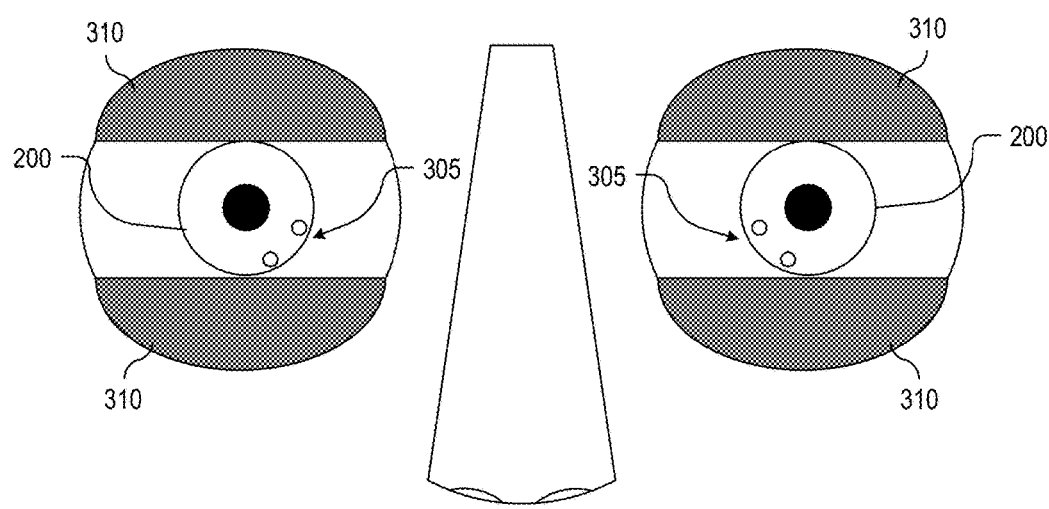
FIGS. 3A and 3B illustrate the general operation of a gaze detection mechanism, in accordance with an embodiment of the disclosure.
Figure 3B:
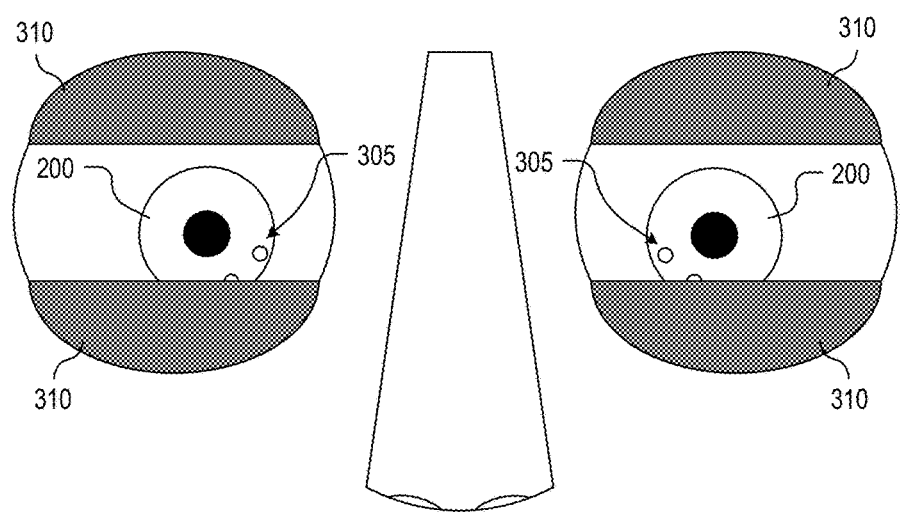

Sensor system 235 is distributed at least partially about eye-mountable device 200 to sense eyelid overlap based on photodetection. By monitoring the amount and position of eyelid overlap, feedback signals from sensor system 235 may be measured by controller 225 to determine the approximate gaze direction and/or focal distance. Referring to FIG. 3A, eye-mountable device 200 is disposed on a cornea that is looking straight forward. In this position, at least two light sensors 305 are not overlapped by eyelids 310, which influences their exposure to light. Controller 225 may determine that the cornea is looking straight forward via the feedback signals from sensors 305. In this scenario, controller 224 may determine that the user is focusing on the far-field and the accommodation adjusted accordingly. Correspondingly (see FIG. 3B), if controller 225 determines, based upon the amount and locations of eyelid 310 overlap of one of sensors 305, that the cornea is looking down and/or inward towards the nose, then it can be assumed the user is focusing on the near-field (e.g., reading). In this scenario, the amount of accommodation applied by accommodation actuator 230 should correspond to a near-field focal distance associated with the activity of reading.

Sensor system 235 is disposed within enclosure material 210 on substrate 215. In the illustrated embodiment, sensor system 235 is distributed peripherally around accommodation actuator 230. In the illustrated embodiment, sensor system 235 is disposed along the inner edge of substrate 215 between antenna 240 and accommodation actuator 230. In other embodiments, sensor system 235 may be partially or entirely distributed along the outer edge of substrate 215 peripherally to antenna 240. Sensor system 235 may be disposed on the backside of substrate 215 adjacent to concave surface 211 or on the frontside of substrate 215 adjacent to convex surface 212. Several orientations, groupings, and distributions may be used to implement sensor system 235. In the illustrated embodiment, sensor system 235 includes a plurality of discrete photodetector sensors distributed at a same distance from a center of enclosure material 210; however, various implementations include photodetectors at different respective distances from such a center. Some implementations for a gaze tracking mechanism, such as one including sensor system 235, are discussed in further detail below in connection with FIGS. 6A, 6B.

Accommodation actuator 230 is centrally positioned within enclosure material 210 to affect the optical power of eye-mountable device 200 in the user's center of vision. In various embodiments, accommodation actuator 230 operates by changing is index of refraction under the influence of controller 225. By changing its refractive index, the net optical power of the curved surfaces of eye-mountable device 200 is altered, thereby applying controllable accommodation. Accommodation actuator 230 may be implemented using a variety of different electro-active optical devices. For example, accommodation actuator 230 may be implemented using a layer of liquid crystal (e.g., a liquid crystal cell) disposed in the center of enclosure material 210. In other embodiments, accommodation actuator 230 may be implemented using other types of electro-active optical materials such as electro-optic materials that vary refractive index in the presence of an applied electric field. Accommodation actuator 230 may be a distinct device embedded within enclosure material 210 (e.g., liquid crystal cell), or a bulk material having a controllable refractive index. In yet another embodiment, accommodation actuator 230 may be implemented using a deformable lens structure that changes shape under the influence of an electrical signal. Accordingly, the optical power of eye-mountable device 200 is controlled by controller 225 with the application of electric signals via one or more electrodes extending from controller 225 to accommodation actuator 230.

Accommodation actuator 230 may be implemented using a variety of different liquid crystal structures including nematic liquid crystal, nematic twisted liquid crystal, cholesteric liquid crystal, or blue phase liquid crystal. Since a low switching voltage is desirable for low power chip design, nematic liquid crystals with switching voltages less than 5 V are suitable. With the application of a 5V control signal, refractive index switching ranging from approximately 1.74 in an off-mode to 1.52 in an on-mode is achievable. A refractive index shift of 0.2 should be sufficient to provide near-field accommodation for reading.

Returning to FIG. 2A, loop antenna 240 is a layer of conductive material patterned along the flat surface of the substrate to form a flat conductive ring. In some examples, to allow additional flexibility along the curvature of the enclosure material, loop antenna 240 may include multiple substantially concentric sections electrically joined together. Each section may then flex independently along the concave/convex curvature of eye-mountable device 200. In some examples, loop antenna 240 may be formed without making a complete loop. For instances, antenna 240 may have a cutout to allow room for controller 225 and power supply 220, as illustrated in FIG. 2A. However, loop antenna 240 may also be arranged as a continuous strip of conductive material that wraps entirely around the flat surface of substrate 215 one or more times. For example, a strip of conductive material with multiple windings may be patterned on the backside of substrate 215 opposite controller 225, power supply 220, and sensor system 235. Interconnects between the ends of such a wound antenna (e.g., the antenna leads) may then be passed through substrate 215 to controller 225.

Since eye-mountable device 100 may be used by different user's having a variety of different eye sizes and eyelid shapes, a configuration process may be useful to train the system for a particular user. Accordingly, a gaze detection calibration may be executed upon an initial use (or even on a periodic basis) to acquire baseline readings for different gaze directions and focal distances.

Figure 4:
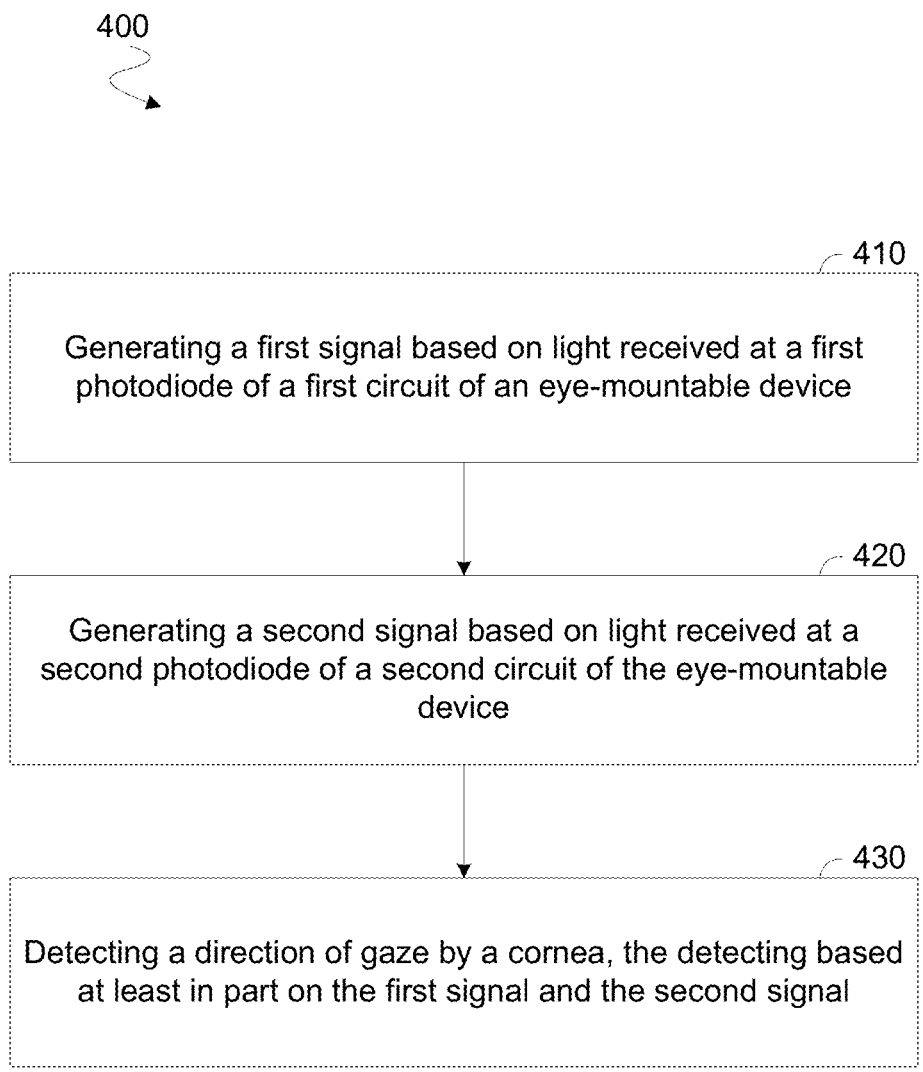
FIG. 4 is a flow chart illustrating a process of gaze tracking based upon photodetection, in accordance with an embodiment of the disclosure.

FIG. 4 illustrates elements of a method 400 for detecting gazing by a user of an EMD according to an embodiment. Method 400 may be performed, for example, by EMD 100, EMD 200 or any of various other eye-mountable devices discussed herein. To illustrate features of various embodiments, method 400 is described herein with respect to a sensor system 500 shown in FIG. 5A. However, such description may be extended to additionally or alternatively apply to another sensor system 550 shown in FIG. 5B, or any of a variety of other such sensor systems according to different embodiments.

Figure 5A:
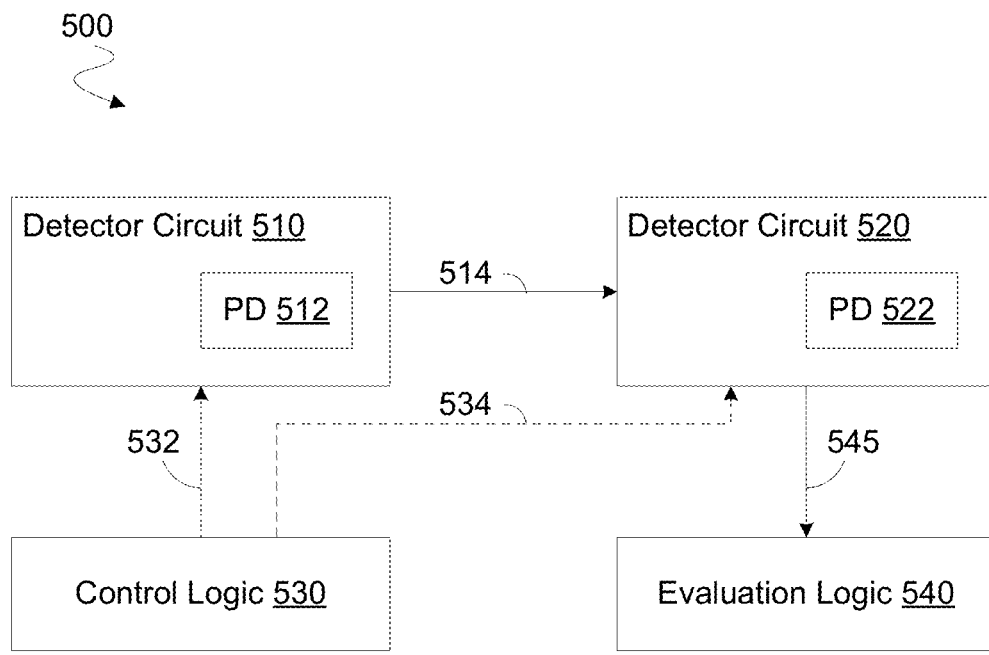
FIGS. 5A and 5B are functional block diagrams of respective sensor systems for an eye-mountable device, each in accordance with a corresponding embodiment of the disclosure.

As illustrated in FIG. 5A, sensor system 500 comprises detector circuits 510, 512 including respective photodiodes 512, 522 each to perform detection of light while sensor system 500 is disposed on a cornea of a user. Detector circuit 510 may operate, for example, in response to one or more control signals 532 that, for example, are provided by the illustrative control logic 530 of sensor system 500 (e.g., where control logic 530 is included in control logic 170). Alternatively or in addition, detector circuit 520 may operate in response to one or more control signals 534 that, for example, are provided by the control logic 530 (or other circuitry of sensor system 500). Such control signals 532, 534 may variously determine respective biasing, switching and/or other operational characteristics of detector circuits 510, 520.

Method 400 may comprise, at 410, generating a first signal based on light received at a first photodiode (PD) of a first circuit of the EMD—e.g., where the generating at 410 includes generating first signal 514 based on light received at PD 512 of detector circuit 510. For example, detector circuit 510 may further comprise a first capacitive load (not shown) that is coupled to variously store different levels of charge at different times. At a given time, a level of the stored charge may be based at least in part on operation of PD 512—e.g., where a charging of and/or discharging from the first capacitive load is determined at least in part by a voltage across PD 512 and/or a current output by PD 512. In such an embodiment, detector circuit 510 may further include sampler circuitry (not shown) to sample a voltage across the first capacitive load and/or a current output by the first capacitive load. Detector circuit 510 may generate first signal 514 based on such sampling—e.g. where the sampler circuitry includes analog-to-digital converter (ADC) circuitry to generate digital information of first signal 514. Although some embodiments are not limited in this regard, a signal (e.g., voltage or current) level, signal frequency, digital value or other characteristic of first signal 514 may be determined by such ADC circuitry. In other embodiments, first signal 514 is an analog output of detector circuit 510.

Method 400 may further comprise, at 420, generating a second signal based on light received at a second PD of a second circuit of the EMD. The first circuit (e.g., detector circuit 510) may be configured to provide a first light response profile, where the second circuit (e.g., detector circuit 520) is configured to provide a second light response profile that is more linear than the first response profile. As used herein in the context of a photodiode (or a detector circuit including such a photodiode), "light response profile" refers to a range of responses by the photodiode (detector circuit) across a domain of levels of light that is incident upon the photodiode. By way of illustration and not limitation, such a range of responses may include a range of values for a voltage across the photodiode and/or a range of values for a current output by the photodiode. Although certain embodiments are not limited in this regard, at least part of the first response profile may be logarithmic or otherwise nonlinear. The non-linearity of the first response profile may facilitate accurate gaze detection that accounts for a wide range of possible lighting conditions of a surrounding environment. By way of illustration and not limitation, a range of lighting intensity levels that varies across several orders of magnitude may correspond to a range of values for a voltage, current and/or other operational characteristic of the first circuit, where the range of values is within fewer orders of magnitude (e.g., within a single order of magnitude).

In the example of sensor system 500, detector circuit 520 further comprises a second capacitive load (not shown) that is coupled to variously store different levels of charge at different times. At a given time, a level of the stored charge may be based at least in part on operation of PD 522—e.g., where a charging of and/or discharging from the second capacitive load is determined at least in part by a voltage across PD 522 and/or a current output by PD 522. Detector circuit 520 further includes sampler circuitry (not shown) to sample a voltage across the second capacitive load and/or a current output by the second capacitive load. In such an embodiment, the generating at 420 may include detector circuit 520 generating second signal 545 based on such sampling—e.g. where the sampler circuitry includes analog-to-digital converter (ADC) circuitry to generate digital information of second signal 545. Although some embodiments are not limited in this regard, a voltage level, frequency, digital value or other characteristic of second signal 545 may be determined by such ADC circuitry. In other embodiments, second signal 545 is an analog output of detector circuit 520.

Method 400 further comprises, at 430, detecting a direction of gaze by a cornea of the user of the EMD. The detecting at 430 is based at least in part on the first signal generated at 410 and the second signal generated at 420. In the example of sensor system 500, first signal 514 is provided to tune or otherwise configure an operation of detector circuit 520 based on a level of light detected with PD 512. By way of illustration and not limitation, configuring of detector circuit 520 with first signal 514 may include setting a voltage, charge, sampling duration, sampling frequency and/or any of various other operational characteristics based on a detection by PD 512 of a current level of ambient light in a surrounding environment. Such configuring of detector circuit 520 with first signal 514 may be a basis for how second signal 545 is generated in response to light sensing by PD 522.

In one embodiment, it is because the second signal is based on first signal that the direction of gaze is detected at 430 based, at least in part, on the first signal. For example, the detecting at 430 may include sending to evaluation logic 540 of sensor system 500 a second signal 545 that is based on first signal 514 (e.g., the first signal generated at 410) and further based on light sensing by PD 522. Evaluation logic 540 may evaluate second signal 545 to detect one or more characteristics of gazing by a user of an EMD including sensor system 500. For example, circuitry of evaluation logic 540 may compare information represented by second signal 545 to a predetermined threshold or other reference value. Such a value may be provided as an a priori parameter—e.g., where the parameter is determined according to conventional gaze detection techniques that are not detailed herein and are not limiting on certain embodiments. Based on evaluation of second signal 545, evaluation logic 540 may detect a direction of gaze—e.g., relative to the position of an eyelid of the user. For example, evaluation logic 540 may detect whether (or not) PD 522 is currently overlapped by an eyelid of a user.

Figure 5B:
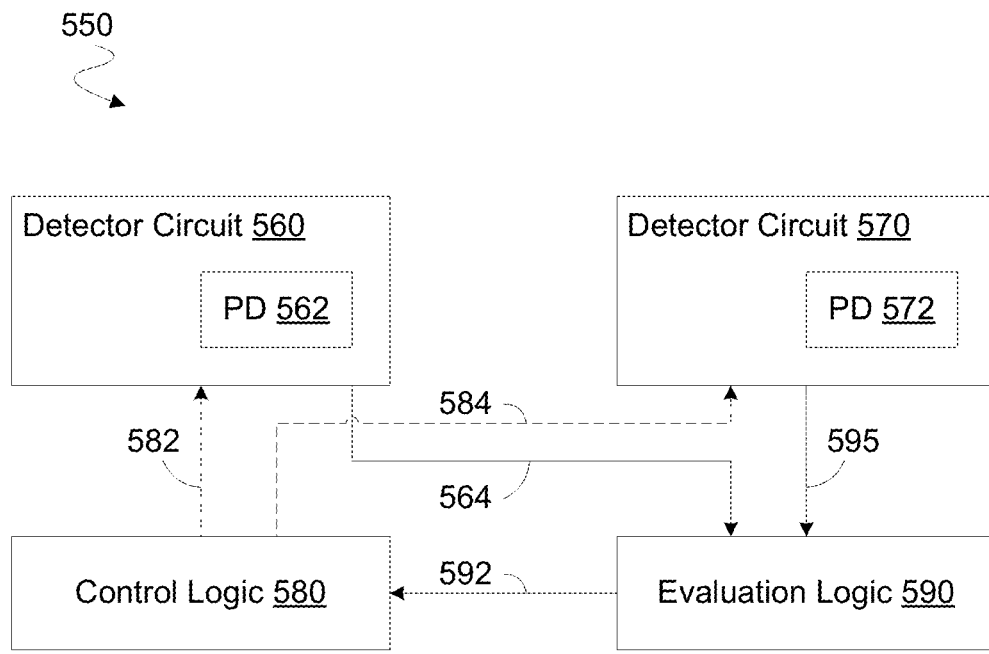

In another embodiment, the direction of gaze is detected at 430 based on the first signal and further based on the second signal, where the first signal is not provided to a detector circuit that generates the second signal. For example, FIG. 5B illustrates a sensor system 550 of an EMD according to another embodiment. Sensor system 550 includes a detector circuit 560, detector circuit 570, control logic 580 and evaluation logic 590 that, respectively, correspond functionally to detector circuit 510, detector circuit 520, control logic 530 and evaluation logic 540. Detector circuits 560, 570 include respective PDs 562, 572 that correspond to PDs 512, 522—e.g., where a light response profile of detector circuit 570 is more linear than a corresponding light response profile of detector circuit 560. Control logic 580 provides one or more control signals 582 and one or more control signals 584 to variously control biasing, switching and/or other operational characteristics of detector circuits 560, 570. Based on such control, light sensing by detector circuit 560 results in a first signal 564 being generated, and light sensing by detector circuit 570 results in a second signal 595 being generated.

In the illustrative embodiment of sensor system 550, the detecting at 430 includes evaluation logic 590 processing a second signal 595 that is generated independent of first signal 564. First signal 564 is provided to evaluation logic 590 as an indication of a current level of light in the surrounding environment. Evaluation logic 590 may adjust a threshold or other parameter that is used as a reference value for evaluating second signal 595. In one embodiment, the first signal 564 and second signal 595 are generated independent of one another. In another embodiment, evaluation logic 590 provides a feedback signal 592 to change operation of detector circuit 570 based on first signal 564, wherein control logic 580 adjusts one or more control signals 570 in response to signal 592, thus changing or otherwise determining how detector circuit 570 generates second signal 595.

FIGS. 6A, 6B illustrate different sensor layouts for implementing a sensor system of an eye-mountable device, in accordance with various embodiments. These sensor systems represent, for example, possible implementations of sensor systems 135, 235, 500. FIG. 6A illustrates a sensor system 600 disposed within an eye-mountable device 620 that, for example, includes features of one of EMDs 100, 200. Operation of EMD 620 may include performing some or all of method 400—e.g., where sensor system 600 operates in aid of determining an optical strength (such as a focal length) to be provided with an accommodation actuator 615 of EMD 620.

In an embodiment, sensor system 600 includes a controller 610 (e.g., comprising logic of controller 125) and at least two photodiodes coupled thereto. By way of illustration and not limitation, controller 610 may be variously coupled via one or more traces 630 to photodiodes 640, 645. The one or more traces 630 may enable respective operation of PDs 640, 645 by providing some or all of a reference potential (e.g., ground), a supply voltage, one or more control signals and/or the like. One or more traces 630 may further provide for one or more signals to be communicated to controller 610. In some embodiments, PDs 640, 645 exchange one or more signals with one another—e.g., via one or more traces 630 (or other such trace). Such an exchange between PDs 640, 645 may be via a path that is independent of controller 610.

One of PDs 640, 645 may be configured to provide a light response profile that is more linear than a corresponding light response profile for which the other of PDs 640, 645 is configured. For example, PDs 640, 645 may provide the corresponding functionality of PDs 522, 512, respectively. In such an embodiment, photodetection by PD 645 may result in a first detector circuit of sensor system 600 configuring (e.g., including a tuning, biasing, or the like) another detector circuit that includes PD 640. Such detector circuitry may be variously located at PDs 640, 645 or, in another embodiment, in controller 610.

A location of PD 645 in EMD 620 may provide for PD 645 to be more exposed, over time, to ambient light of a surrounding environment (e.g., as compared to the amount of such exposure over time for EMD 640). In the illustrative embodiment shown, PD 645 is closer than PD 640 to a center of EMD 620, whereby PD 640 is—as compared to PD 645—more likely be covered at different times by an eyelid of a user. When the cornea of the user moves, an eyelid overlap of PD 640 may cause a signal (e.g., signal 545) to be generated by detector circuitry that includes PD 640. Such detector circuitry may be configured based on a concurrent or earlier light detection by PD 645. Different signal levels, frequencies, values or other characteristics of such a signal may be associated with different gazing directions and/or focal distances and may thereby be used—e.g., by controller 610—to determine a user's gazing direction and/or focal distance.

FIG. 6B illustrates another sensor system 650 disposed within an eye-mountable device 670 that, for example, includes features of one of EMDs 100, 200. Operation of EMD 670 may include performing some or all of method 400—e.g., where sensor system 650 operates in aid of determining an optical strength to be provided with accommodation actuator 665. Sensor system 650 may include features similar to those of sensor system 600. For example, sensor system 650 may include a controller 660, one or more traces 680 and PDs 690, 695 that correspond functionally to, controller 610, one or more traces 630 and PDs 640, 645, respectively.

One of PDs 690, 695 may be configured to provide a light response profile that is more linear than a corresponding light response profile for which the other of PDs 690, 695 is configured. For example, PDs 690, 695 may provide the corresponding functionality of PDs 522, 512, respectively. In such an embodiment, photodetection by PD 695 may result in a first detector circuit of sensor system 600 configuring (e.g., including a tuning, biasing, or the like) another detector circuit that includes PD 690. Such detector circuitry may be variously located at PDs 690, 695 or, in another embodiment, in controller 660.

A location of PD 695 in EMD 670 may provide for PD 695 to be more exposed, over time, to ambient light of a surrounding environment (e.g., as compared to the amount of such exposure over time for EMD 690). In the illustrative embodiment shown, PDs 690, 695 are rotationally offset from one another—e.g., by at least forty-five (45) degrees—with respect to a center of EMD 670. In such an embodiment, EMD 670 may include a weighted structure, toric structure or other such mechanisms to provide for automatic orientation and/or rotational stability on an eye of the user. Such mechanisms may increase the likelihood that EMD 690 is, over time, closer than EMD 695 to an eyelid of a user. When the cornea of the user moves, an eyelid overlap of PD 690 may cause a signal (e.g., signal 545) to be generated by detector circuitry that includes PD 690. Such detector circuitry may be configured to generate the signal based on a concurrent or earlier light detection by PD 695. Different characteristics of such a signal may be associated with different gazing directions and/or focal distances and may thereby be used—e.g., by controller 610—to determine a user's gazing direction and/or focal distance.

Figure 7A:
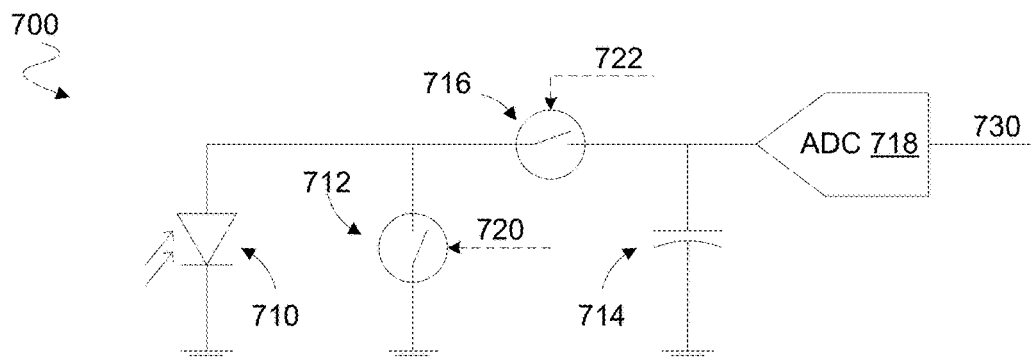
FIGS. 7A and 7B are circuit diagrams illustrating respective detector circuits of a gaze tracking system each according to a respective embodiment of the disclosure.

FIG. 7A shows features of a detector circuit 700 to aid in gaze detection by an eye-mountable device according to an embodiment. Detector circuit 700 may include some or all of the features of detector circuit 510, for example. Detector circuit 700 is just one example of a circuit including a photodiode and other circuitry to perform sampling of a voltage, current or other characteristic that is based on photodetection by the photodiode.

In the illustrative embodiment shown, detector circuit 700 includes a photodiode 710 that is forward biased for PD 710—and/or detector circuit 700 as a whole—to provide some non-linear (e.g., logarithmic) light response profile. An example of such a response profile is illustrated conceptually in graph 780 of FIG. 7C by an idealized relationship 786 between a sample voltage 782—generated with a PD—and a level of light 784 that is incident upon that PD. Relationship 786 may represent a response profile for a voltage across PD 710, a voltage across capacitor 714 after a given period of charging by PD 710 or any of a variety of other operational characteristic based on light sensing by PD 710. The illustrative relationship 786 is substantially logarithmic at least in a domain above a level 10 of light incident upon PD 710. Certain embodiments are not limited to particular voltages or light levels of relationship 786, which may vary widely according to implementation-specific details.

In an embodiment, detector circuit 700 includes a capacitive load—as represented by the illustrative capacitor 714—and circuitry to selectively couple the capacitive load to the PD 710. Detector circuit 700 may further comprise an analog-to-digital converter (ADC) 718 to sample the charge in capacitor 714 (e.g., including sampling a voltage across capacitor 714) and to generate a digital signal 730 based on an amount of such charge. Operation of detector circuit 700 may include closing switches 712, 716 (e.g., with respective control signals 720, 722) to set/reset detector circuit 700 to a baseline state by decreasing any voltage across PD 710 and capacitor 714. Subsequently, switch 712 may be opened (while switch 716 remains closed) to allow for PD 710 to begin charging capacitor 714. A rate at which capacitor 714 charges may depend upon a current level of light incident upon PD 710. After some a priori period of time determined by control signal 722, switch 716 may be opened to stop the charging of capacitor 714, and ADC 718 may then sample the amount of such charge. A particular level, frequency, value or other characteristic of output 730 may thus indicate the level of light incident on PD 710.

Figure 7B:
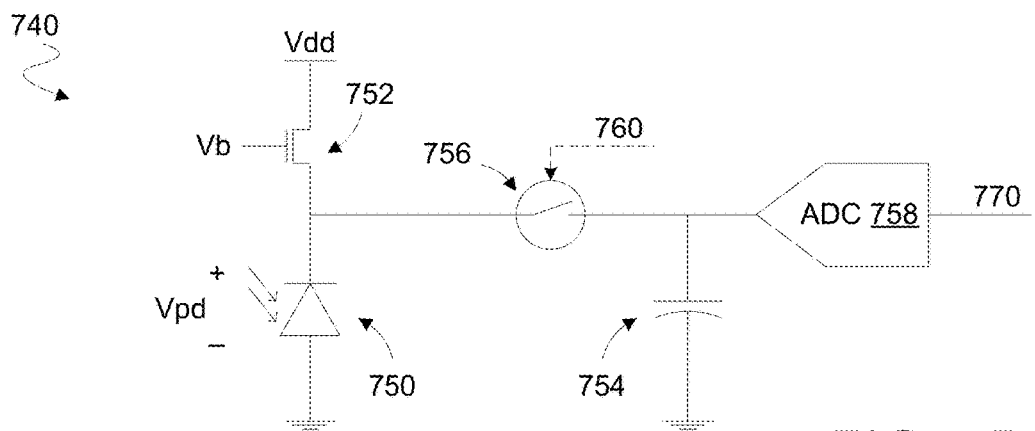
Figure 7C:
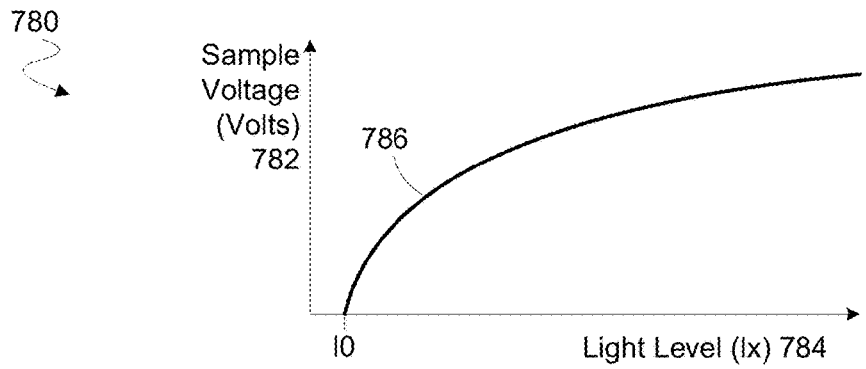
FIG. 7C is a graph illustrating a light response profile of a detector circuit for a gaze tracking system according to an embodiment of the disclosure.

FIG. 7B shows features of a detector circuit 740 to aid in gaze detection by an eye-mountable device according to another embodiment. Detector circuit 740 may include some or all of the features of detector circuit 510, for example. Detector circuit 740 is another example of a circuit configured to provide a logarithmic or other non-linear light response profile—e.g., according to relationship 786.

Detector circuit 740 may include a PD 750, a transistor 752 coupled between PD 750 and a supply voltage Vdd, a capacitor 754 and a switch 756 to selectively couple capacitor 754 to PD 750. Detector circuit 740 may further comprise an analog-to-digital converter (ADC) 758 to sample charge in capacitor 754 and generate a digital signal 770 based on an amount of such charge. In an embodiment, detector circuit 740 may be set (e.g., reset) to some initial state in preparation for operation to sense light with PD 750. For example, such initialization may include turning off transistor 752 (e.g., setting bias voltage Vb to 0V temporarily) and allowing PD 750 to discharge capacitor 754 while switch 756 is closed.

During subsequent light sensing by detector circuit 740 while transistor 752 is biased, a voltage $V_{pd}$ across PD 750 may be represented by the following equation:

$$V_{pd} = (k)\left[\ln\left(\frac{(I_b + i_{ph})}{I_o}\right)\right]$$

where $I_b$ is a component of the current through transistor 752 that is induced by due to Vb, $i_{ph}$ is a component of the current through transistor 752 that is induced by PD 750, $I_o$ is a reverse saturation current for transistor 752 and k is a constant. In one illustrative embodiment, transistor 752 is an n-channel metal-oxide-semiconductor (NMOS) field effect transistor that is biased by Vb to be below its threshold state. Consequently, detector circuit 740 may provide a substantially logarithmic light response profile. Operation of detector circuit 740 may include closing a switch 756 (e.g., based on a control signal 760) to allow for PD 750 to begin charging capacitor 754. After some a priori period of time determined by control signal 760, switch 756 may be opened to stop the charging of capacitor 754, and ADC 758 may then sample the amount of such charge and generate a digital signal 770 based on such sampling. In another embodiment, switch 760 remains closed and ADC 758 continuously samples capacitor 754.

Figure 8A:
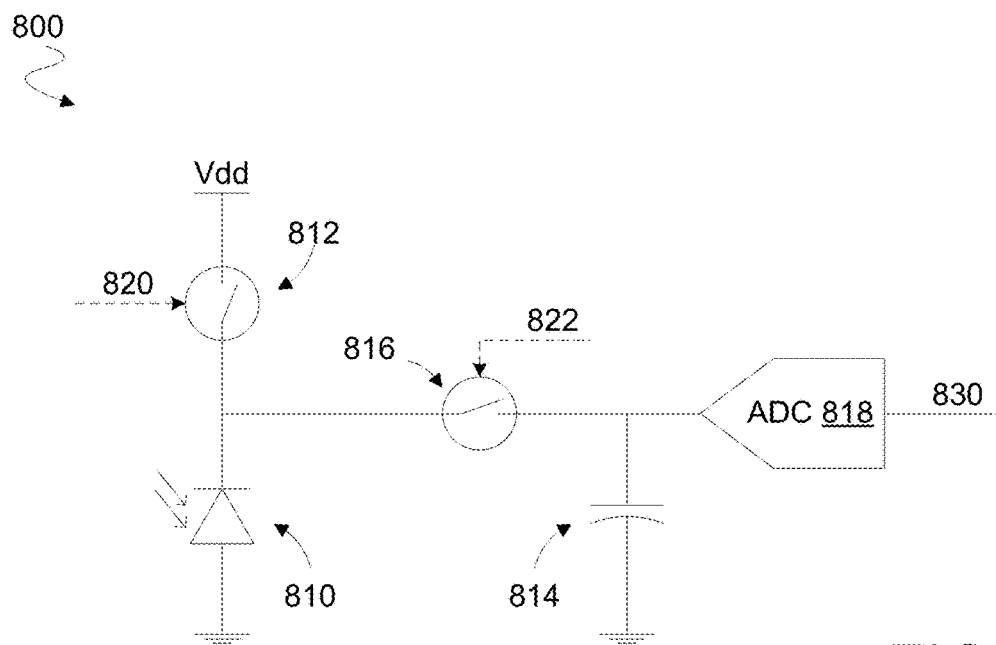
FIG. 8A is a circuit diagram illustrating a detector of a gaze tracking system according to an embodiment of the disclosure.

FIG. 8A shows features of a detector circuit 800 to aid in gaze detection by an eye-mountable device according to an embodiment. Detector circuit 800 may include some or all of the features of detector circuit 520, for example. Detector circuit 800 is one example of a circuit including a photodiode and other circuitry to perform sampling that is based on photodetection by the photodiode. In the illustrative embodiment shown, detector circuit 800 includes a PD 810, a switch 812 coupled between PD 810 and a supply voltage Vdd, a capacitor 814 and a switch 816 to selectively couple capacitor 814 to PD 810. Detector circuit 800 may further comprise an analog-to-digital converter (ADC) 818 to sample charge in capacitor 814 and generate a digital signal 830 based on an amount of such charge.

Detector circuit 800 may be configured to aid in detector circuit 800 providing a relatively linear light response profile. In the embodiment illustrated by FIG. 8A, PD 810 is reverse biased to aid in PD 810—and/or detector circuit 800 as a whole—providing some light response profile that is relatively linear, as compared to a light response profile of another detector circuit (such as one of detector circuits 700, 740). A signal from the other detector circuit may configure detector circuit 800 to provide a particular one of multiple, comparatively linear, light response profiles. By way of illustration and not limitation, detector circuit 800 may be coupled to another detector circuit (not shown) that generates an output based on photodetection by that other detector circuit. Control signal 822 (or other signal to configure detector circuit 800) may include or otherwise be based on such an output signal. For example, a sampling period, sampling frequency or other operational characteristic of switch 816 may be determined based at least in part on a detection by the other detector circuit of a level of ambient light in a surrounding environment.

Figure 8B:
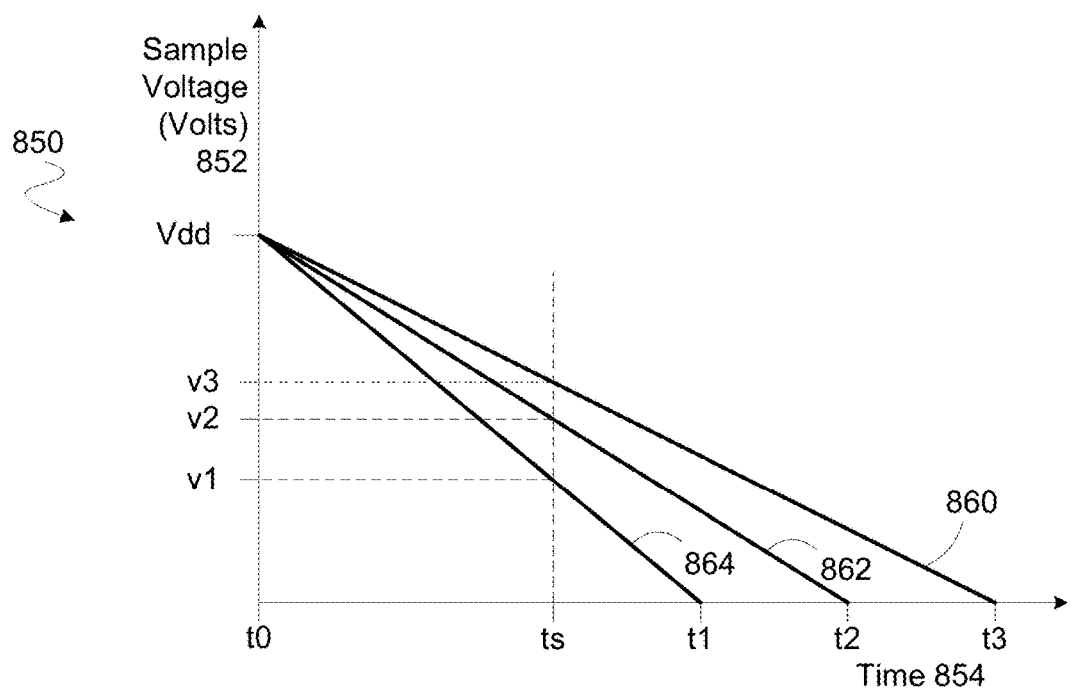
FIG. 8B is a graph illustrating various outputs by a detector circuit for a gaze tracking system according to an embodiment of the disclosure.

FIG. 8B shows a graph 850 of various transitions 860, 862, 864 of a sample voltage 852 (e.g., across capacitor 814) over time 854, the transitions 860, 862, 864 each corresponding to a different respective level of illumination sensed at PD 810. The relationship between sample voltage 852 and a range of such illumination levels may be relatively linear—e.g., as compared to a light response profile of one of circuits 700, 740. Although transitions 860, 862, 864 are each shown as starting at a time t0 for the sake of comparison, it will be appreciated that PD 810 is exposed to only such level of illumination at a given time.

In graph 850, a time t0 coincides with switch 812 opening, when capacitor 814 has been charged to provide sample voltage 852 at some initial level (e.g., the level of supply voltage Vdd). After switch 812 opens (and switch 816 is closed), capacitor 814 will discharge while coupled to PD 810, where a relatively higher level of illumination at PD 810 results in a relatively faster discharge of sample voltage 852. In an illustrative scenario according to one embodiment, a dark (e.g., nighttime) lighting environment results in a relatively slow discharge time, where detector circuit 800 thus provides transition 860. By contrast, a bright (e.g., daytime) lighting environment may result in a relatively fast discharge time, where detector circuit 800 thus provides transition 864. A moderate (e.g., twilight) lighting environment may result in a middling discharge time such as that represented by transition 862. A voltage sampled at a time $t_s$ (e.g., one of voltages $v_1$, $v_2$, $v_3$) may represent, or otherwise be used to determine, a difference between a level of light incident at PD 810 and a level of light incident upon another PD (e.g., PD 710 or PD 750).

When the cornea of the user moves, an eyelid overlap of PD 810 may result in a level, frequency, value or other characteristic of signal 830 that is based on light detected at 810 and on a configuration of detector circuit 800 in response to concurrent or earlier photodetection by another circuit. Different signal levels, values or other information represented by such a signal may be associated with different gazing directions and/or focal distances and may therefore be used—e.g., by controller 125—to determine a user's gazing direction and/or focal distance. In one embodiment, operation of switch 812 and/or switch 816 is based on a signal from another circuit (e.g., one of circuits 700, 740) indicating a level of environmental illumination that is detected with that other circuit. Alternatively or in addition, such a signal from the other circuit may instead be provided, along with signal 830, to other logic (not shown) for evaluation to detect a direction of gaze by a user.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic system comprising:
   an enclosure that is compatible with an eye;
   a sensor system disposed within the enclosure, the sensor system including:
     a first circuit coupled to generate a first signal in response to light received at a first photodiode (PD), wherein the first circuit is configured to have a first light response profile, the first light response profile being a non-linear response profile, and wherein the first signal indicates a level of ambient light based on the first light response profile; and
     a second circuit coupled to generate a second signal in response to light received at a second PD, wherein the second circuit is configured to have a second light response profile, the second light response profile being a more linear response profile than the first light response profile, wherein the second light response profile is adjusted based on the first signal, and wherein the second signal is generated based on the second light response profile; and
   evaluation logic coupled to the sensor system, the evaluation logic configured to determine, based at least in part on the second signal, a value indicative of an amount of accommodation to be applied by the ophthalmic system.

2. The ophthalmic system of claim 1, wherein the second circuit further includes:
   a capacitive load coupled to receive and store charge generated by the second PD;
   a switch coupled between the capacitive load and the second PD, the switch controlled based on the first signal; and
   a sampler circuit coupled to generate the second signal based on charge stored on the capacitive load.

3. The ophthalmic system of claim 1, wherein the first PD is closer than the second PD to a center of the enclosure.

4. The ophthalmic system of claim 1, wherein the first PD is rotationally offset from the second PD with respect to a center of the enclosure.

5. The ophthalmic system of claim 1, wherein the first circuit further comprises:
   a first capacitive load coupled to store a charge form the first PD; and
   a first sampler circuit coupled to generate the first signal based on the charge stored by the first capacitive load.

6. The ophthalmic system of claim 5, wherein, based on a level of charge stored by the first capacitive load, the first sampler circuit determines one of:
   a voltage level of the first signal;
   a current level of the first signal;
   a frequency of the first signal; or
   a number represented by the first signal.

7. The ophthalmic system of claim 1, wherein the first light response profile is logarithmic.

8. The ophthalmic system of claim 1, wherein the enclosure has a concave surface and a convex surface, wherein the concave surface is configured to be removeably mounted over the eye and the convex surface is configured to be compatible with eyelid motion when the concave surface is so mounted.

9. The ophthalmic system of claim 1, further comprising an accommodation actuator coupled to change an optical power of the ophthalmic system in response to the value indicative of the amount of accommodation.

10. The ophthalmic system of claim 9, wherein the accommodation actuator comprises a see-through electro-active optical material having a refractive index that changes under electrical influence.

11. The ophthalmic system of claim 9, wherein the accommodation actuator comprises a see-through liquid crystal layer having a refractive index that changes under electrical influence.

12. A method of operation of an ophthalmic system, the method comprising:
   generating a first signal in response to light received at a first photodiode (PD) of a first circuit of the ophthalmic system, wherein the first circuit is configured to have a first light response profile, the first light response profile being a non-linear profile, and wherein the first signal indicates a level of ambient light based on the first light response profile;
   configuring a second circuit based on the first signal, wherein the first signal determines a second light response profile of the second circuit, the second light response profile being more linear than the first light response profile and adjusted based upon the first signal;
   generating a second signal based on light received at a second PD of the second circuit of the ophthalmic system, wherein the second signal is generated based on the second light response profile; and
   determining a value indicative of an amount of accommodation to be applied by the ophthalmic system based at least in part on the second signal.

13. The method of claim 12, wherein the second circuit further includes:
   a capacitive load coupled to receive and store charge generated by the second PD;
   a switch coupled between the capacitive load and the second PD, the switch controlled based on the first signal; and
   a sampler circuit coupled to generate the second signal based on charge stored on the capacitive load, and
   wherein configuring a second circuit based on the first signal comprises:
   determining a length of time the switch couples the capacitive load to the second PD to provide the second light response profile.

14. The method of claim 12, wherein the ophthalmic system comprises an eye mountable device and wherein the first PD is closer than the second PD to a center of the eye mountable device.

15. The method of claim 12, wherein the ophthalmic system comprises an eye mountable device and wherein the first PD is rotationally offset from the second PD with respect to a center of the eye mountable device.

16. The method of claim 12, wherein the first circuit further includes a first capacitive load coupled to the first PD, and wherein generating the first signal includes determining, based on a level of charge on the first capacitive load, one of:
   a voltage level of the first signal;
   a current level of the first signal;
   a frequency of the first signal; and
   a number represented by the first signal.

17. The method of claim 12, wherein the second circuit further includes a second capacitive load, wherein the first signal determines a time during which the second capacitive load is coupled to exchange charge with the second PD, and wherein generating the second signal is based on charge stored by the second capacitive load.

18. The method of claim 12, further comprising:
changing the amount of accommodation of the ophthalmic system based upon the value.

* * * * *